Figure 1:
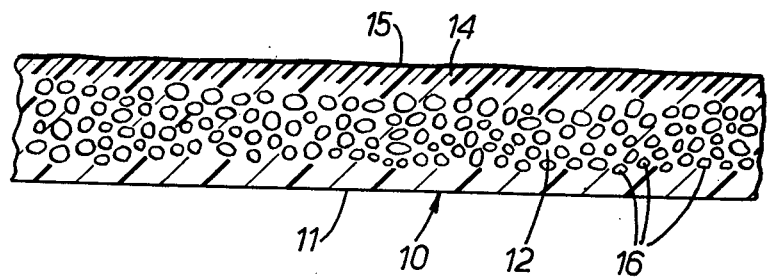

United States Patent [19]
Lock et al.

[11] 4,233,969
[45] Nov. 18, 1980

[54] WOUND DRESSING MATERIALS

[76] Inventors: Peter M. Lock, 327 Lordswood La., Petrosa, Walderslade, Chatham, Kent; David R. Webb, 9 Lambourn Way, Lordwood, Chatham, Kent, both of England

[21] Appl. No.: 850,375

[22] Filed: Nov. 10, 1977

[30] Foreign Application Priority Data

Nov. 11, 1976 [GB] United Kingdom ............ 47074/76

[51] Int. Cl.³ ............................................ A61L 15/00
[52] U.S. Cl. ................................................... 128/156
[58] Field of Search .................. 128/156, 296; 521/51

[56] References Cited

U.S. PATENT DOCUMENTS

| | | | |
|---|---|---|---|
| 3,157,178 | 11/1964 | Bentov | 128/296 |
| 3,648,692 | 3/1972 | Wheeler | 128/296 |
| 3,763,858 | 10/1973 | Buese | 128/155 |
| 3,800,792 | 4/1974 | McKnight et al. | 128/156 |
| 3,849,238 | 11/1974 | Gould et al. | 128/156 |
| 3,927,669 | 12/1975 | Glatt | 128/156 |
| 3,949,742 | 4/1976 | Nowakowski | 128/156 |
| 3,972,328 | 8/1976 | Chen | 128/156 |
| 3,975,567 | 8/1976 | Lock | 521/51 |

FOREIGN PATENT DOCUMENTS

1429711  3/1976  United Kingdom .

*Primary Examiner*—C. Fred Rosenbaum
*Attorney, Agent, or Firm*—Burns, Doane, Swecker & Mathis

[57] ABSTRACT

A wound dressing material, particularly for burns, comprises a sheet of synthetic plastics material which is permeable to water vapor and air, preferably a polyurethane produced by polymerization of an isocyanate capped polyoxyethylene polyol, without any substantial amount of water present, using a cross-linking agent which reacts with the isocyanate groups. The polyol and cross-linking agent, and preferably also an alkylene oxide surfactant, are agitated to form an aerated mix, spread on a release paper, and heated so that polymerization begins in the exposed upper surface, so as to form a sheet having a dense outer region which is impervious to liquids, a cellular region beneath the dense region, and a smooth glazed surface for application to a wound.

10 Claims, 3 Drawing Figures

WOUND DRESSING MATERIALS

This invention relates to wound dressing materials, and more specifically to a material which can be applied to many types of injury or wound but is particularly useful as a temporary wound cover in the therapeutic treatment of burns, varicose ulcers, pressure areas and other related injuries. The term "burns" covers thermal, chemical, electrical and similarly inflicted wounds involving skin damage or destruction.

Burns require a unique combination of therapy and dressing when the function of the skin is absent or impaired, because nutritious body fluids and their essential components are continuously lost through the wound, which in the case of a large area burn can cause dehydration of the patient and in turn involve more serious complications such as lung and kidney malfunctions, while the normal protection provided by the skin from invading harmful bacteria and other toxic and noxious agents is no longer available.

Many types of dressing material having been used heretofore. Absorbent fibrous materials such as cotton gauze can cause excessive dehydration and drying of the wound and thus become firmly adhered to the affected area, so that dressing changes are painful and can cause further damage to the wound. The natural healing process in which skin cells multiply and migrate across the moist wound surface is delayed, because the cells have to burrow deep under the dried area. Individual fibres can also become detached from the dressing and embedded in the wound and thereby impede healing.

To prevent adherence and maintain a moist wound environment, dressing materials impregnated with greasy substances such as petroleum jelly have been employed. These dressings require frequent changing to avoid drying out, with consequent frequent exposure of the wound to airborne bacteria, and the greasy substances provide a good environment for the proliferation of bacteria so that wound infection is difficult to avoid, while the greasy substances can also be absorbed into the wound and retard healing by acting as foreign bodies.

Dressings made of polyethylene, polypropylene and polyamide films eliminate adherence of the dressing to the wound and prevent particles being embedded therein, but being non-porous they cannot absorb the excess of liquid exudate which exudes from a burn and they can therefore become painful to the patient unless changed frequently, with consequent exposure of the wound to airborne bacteria. The micro-climate under such film dressings, while favourable for healing, is also ideal for such bacteria so that wound infection again becomes a problem, while the fact that the condition of the wound is visible through the film dressing is depressing to the patient. Other film dressing materials made of gelatins, alginates and celluloses have been designed to create the same favourable micro-climate in the wound by dissolving or melting in the exudate and re-forming as part of the eschar (scab). This increases wound dehydration and the films, when mixed with the exudate in the eschar, become supportive of bacteria but cannot be removed from the wound because they have become an integral part of it. Even if infection is avoided, the dehydration effect delays healing. Plastic spray-on dressings involve similar problems, particularly encapsulation of dressing material deep in the wound.

Absorbent dressings of polyvinyl alcohol sponge and of polyurethane foam with an open cell structure have been found to cause wound dehydration and adherence of the dressing to the wound, while small particles of the cells of the dressing material can become detached and embedded in the wound, causing undesirable reactions. Also, passage of the exudate right through the dressing can provide a nutrient path for airborne bacteria back through the dressing into the wound. A polyurethane foam dressing with an impermeable backing of polytetrafluoroethylene avoids the latter problem but still suffers from the problem of detached particles.

Biological wound covers, mainly of porcine and cadaver skin, perform well in many respects but suffer from the problem that it is extremely difficult to avoid leaving small fragments of dermis in the wound when removing the dressing, producing subsequent foreign body reactions which can cause rejection of autografts and later breakdown of healed wounds, and causing production of antibodies which might involve serious consequences at a later date.

An object of the present invention is to provide a wound dressing material which is free from the disadvantages of the known materials described above.

According to the present invention, a wound dressing material comprises a sheet of a synthetic plastics material which is permeable to water vapour and to air, having on one side a smooth glazed surface for application to a wound, a cellular region behind the smooth surface, and a more dense region behind the other surface, so that on contact with liquid exudate from a wound the dressing material will absorb a limited amount of exudate but prevent it from passing right through the dressing material.

The fact that the dressing material is water vapour- and air-permeable, but will not permit the liquid exudate to pass through it, assists in maintaining a moist micro-climate favourable for healing in the wound. The smooth glazed surface avoids the danger of detachment of cell particles and assists in preventing adherence of the dressing to the wound. The cellular region enables the dressing to absorb excess of liquid exudate without drawing out so much exudate that the wound would become dried and the patient dehydrated. Dressings need not be changed too frequently.

Preferably the synthetic plastics material is a polyurethane, in particular the product of polymerisation of an isocyanate capped polyoxyethylene polyol employing a cross-linking agent or catalyst which is reactive with the isocyanate groups, without any substantial amount of water present. The synthetic plastics material preferably also incorporates an alkylene oxide surfactant to increase the hydrophilic nature of the dressing material.

The cross-linking agent or catalyst preferably contains in its molecule two or more amine and/or hydroxyl groups which are reactive with the isocyanate groups.

In the preferred embodiment, the polyol is a polyoxyethylene diol having a weight average molecular weight of approximately 1500, containing a proportion of polyols having three or more hydroxyl groups, the diol and polyols having been capped with di-isocyanates. The preferred cross-linking agent or catalyst is dimethylethanolamine. Other cross-linking agents or catalysts may be selected from the group comprising diethylenetriamine, triethylenetetramine, tetraethylenepentamine, polyethyleneimine, glycerol, trimethylolpropane, pentaerythritol, tolylene-2,4,6-triamine, ethylene diamine, amino-ethanol, trimethylenediamine, tetramethylenediamine, pentamethylenediamine, hexamethylenediamine, ethanolamine, diethanolamine, hydrazine, triethanolamine, benzene-1,2,4-tricarboxylic acid, nitrilotriacetic acid, citric acid, 4,4'-methylenebis (o-chloroaniline). The alkylene surfactant may contain ethylene oxide and propylene oxide, and the proportions of these may lie in the range from 75:25% to 40:60% by weight.

The invention also comprehends a method of making a wound dressing material, comprising the steps of mixing an isocyanate capped polyoxyethylene polyol with an alkylene oxide surfactant with agitation to form an aerated creamy mix, incorporating a cross-linking agent or catalyst in the mix, spreading the mix on to a smooth glazed release paper to form a sheet of a predetermined uniform thickness, and heating the sheet to assist polymerization of the mix, with the exclusion of any substantial amount of water from the mix during the said steps and with application of heat in the last mentioned step in such manner that polymerisation is initiated first in the upper surface of the sheet to form a dense outer region which is impervious to liquids while trapping sufficient gases in the region behind the lower surface to render the latter region cellular. Preferably the release paper is supported on a flat surface, such as a sheet of glass, during the spreading and heating steps. The spreading may be effected by means of at least one spreader bar with a corrugated surface which is drawn over the surface of the paper at a fixed distance above it. The heating is preferably effected in an oven using a fan to ensure even application of heated air to the upper surface of the sheet.

Figure 2:
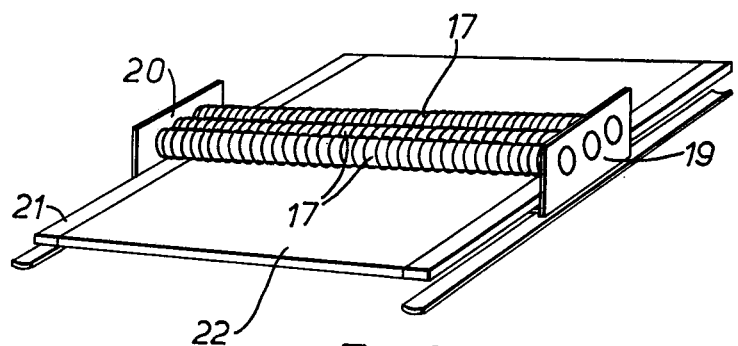
Figure 3:
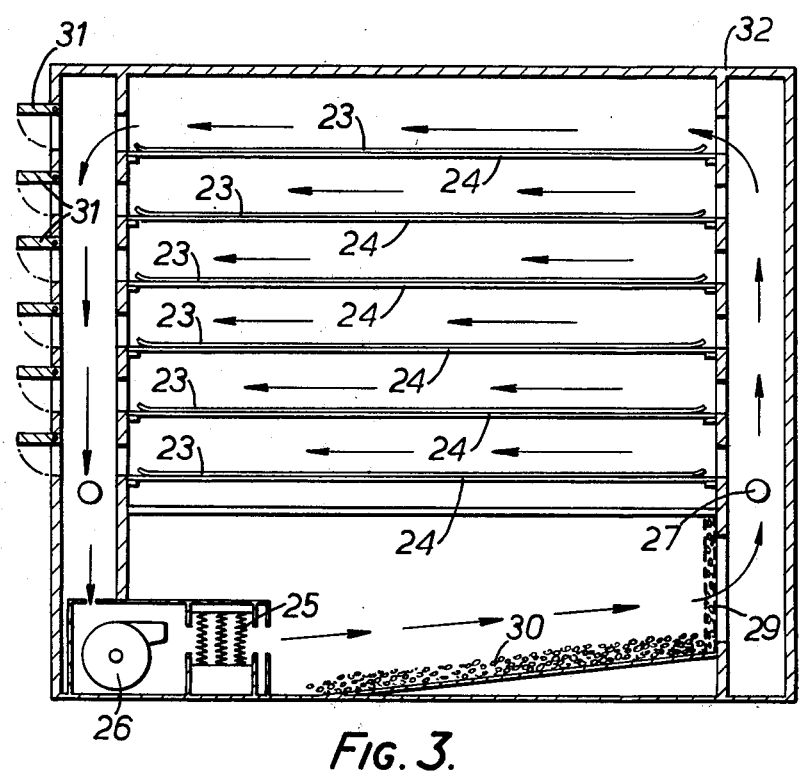

A preferred embodiment of the invention will now be described by way of example and with reference to the accompanying drawings, in which:

FIG. 1 is an enlarged cross-section through an example of a dressing material according to the invention, FIG. 2 is a perspective diagrammatic view of apparatus used in the spreading step in the manufacture of the dressing material, and FIG. 3 is a diagrammatic cross-section of a curing cabinet or oven used to effect heating and polymerisation of the material.

In this preferred embodiment, the dressing material is formed by polymerisation of a polyol supplied by W. R. Grace & Co., of New York, U.S.A., under the Trade Name HYPOL, which is described in British Pat. No. 1429711. The polyol is a polyoxyethylene diol having a weight average molecular weight of approximately 1500, containing a proportion of polyols having three or more hydroxyl groups, the diol and polyols having been capped with di-isocyanates. British Pat. No. 1429711 describes the reaction of the isocyanate capped polyol with water to form a polyurethane foam, and states that, particularly where the isocyanate functionality is only about 2, a cross-linking agent or catalyst should be employed to promote cross-linking of the foamed polymer. The cross-linking agent or catalyst should be polyfunctional and reactive with isocyanate groups and include but are not limited to materials such as diethylenetriamine, triethylenetetramine, tetraethylenepentamine, polyethyleneimine, glycerol, trimethylolpropane, pentaerythritol, tolylene-2,4,6-triamine, ethylene diamine, amino-ethanol, trimethylenediamine, tetramethylenediamine, pentamethylenediamine, hexamethylenediamine, ethanolamine, diethanolamine, hydrazine, triethanolamine, benzene-1,2,4-tricarboxylic acid, nitrilotriacetic acid, citric acid 4,4'-methylenebis(o-chloroaniline).

In the formation of the dressing material according to the present invention, polymerization is effected in the substantially total absence of water and the product, although evidently a polyurethane, is only cellular to a limited extent in one region and is not blown to form a polyurethane foam by water reaction as in the product of British Pat. No. 1429711.

In the production of the preferred embodiment of the dressing material according to the present invention, the HYPOL polyol is polymerized with dimethylethanolamine and incorporates an ethylene oxide/propylene oxide surfactant to increase the hydrophilic nature of the dressing material.

The nature of the dressing material is illustrated in an enlarged cross section in FIG. 1. The dressing material generally indicated at 10 has a smooth, highly glazed surface 11 on the side which is to be applied to a wound, a cellular region 12 behind the smooth surface 11, and a more dense region 14 behind the other surface 15. The cells 16 of the cellular region 12 are substantially smaller than those of a normal plastics foam and are normally closed. The material between the cells 16 in the region 12 is itself porous and hydrophilic, containing very small pores which are much smaller again than the cells 16, so that on contact with an aqueous fluid it absorbs it swells and absorbs at least some of the fluid.

In the production of the dressing material, 100 parts of the HYPOL polyol are mixed with from 0.1 to 5 parts, preferably 1.8 parts, of a surfactant/stabiliser containing 75% ethylene oxide and 25% propylene oxide by weight, using whisk type paddles to form an aerated creamy mix, in an atmosphere of low relative humidity at a temperature between 15° C. and 55° C., preferably 25° C. The mixture is allowed to stand for approximately 3 to 4 minutes to permit escape of large air bubbles trapped during mixing, but should not be left for longer periods to avoid reaction with atmospheric moisture. From 0.1 to 1.5 parts, preferably 0.7 parts, of dimethylethanolamine are then added and mixing is resumed for a further 30 to 60 seconds. The creamed mixture is then poured on to a smooth glazed release paper having a release coating of polyethylene and silicone, which is tightly stretched over a long table having a flat surface, such as a sheet of smooth plate glass ¼ inch thick, to ensure absence of wrinkles, folds or ridges. The creamy mix is then spread over the paper to form a layer of uniform thickness.

A device which has been devised for this purpose is illustrated in FIG. 2 and comprises three parallel stainless steel tubes 17 of 2 inch external diameter which are spaced about 1 inch apart, and each of which is wound externally with 1 mm round stainless steel wire 18 from end to end, the wire being held in position by soldering, to provide a corrugated surface. Alternatively, the tubes 17 may be formed with a screw thread on their external surfaces. The tubes 17 can be rotated in end plates 19, 20 which are mounted on a sled running in tracks on each side of the table. The end plates 19, 20 are of stainless steel and support each end of the tubes 17 so that, the corrugated surfaces of the tubes 17 are maintained at a uniform spacing from the glass sheet 21. The spacing of the tubes 17 from the sheet 21 may be adjusted according to the thickness of the dressing material to be produced, from e.g. 0.25 mm to 3 mm. The normal spacing is 0.75 mm to produce a dressing material 1 mm thick. By traversing the tubes 17 over the creamy mix on the paper 22, the mix is spread into an even layer over the paper while large air bubbles are burst or encouraged to emerge from the mixture. The tubes 17 may be rotated through 120° between traverses over the mix, so that three traverses can be made before the tubes must be removed and cleaned.

A spray head may be employed for pouring the creamed mixture on to the paper 22, with a V-shaped plough to effect preliminary spreading before the tubes 17. This arrangement is not illustrated.

When the spreading has been completed the paper 22 is drawn lengthwise off the glass plate 21 and cut transversely into sections which are received on trays 23 which are then transferred rapidly through louvre doors 31 to a curing cabinet 32 or oven illustrated in FIG. 3, which has a set of glass shelves 24 mounted one above the other to support the trays 23. The cabinet 32 is heated by means of three electrical elements 25 and a fan 26 which circulates the heating air in the directions illustrated by the arrows. Thermostats 27,28 are connected to the heating elements to ensure an even temperature throughout the cabinet. Silica gel is contained in a mesh screen 29 and placed on a sloping ramp 30 in the path of the heated air after it leaves the heating elements 25 before it reaches the glass shelves 24, so as to maintain the relative humidity in the cabinet at a low level, preferably below 10% or at most 20%. The temperature in the curing cabinet is preferably maintained at 150° F., though temperatures between 90° F. and 160° F. can be used in certain circumstances. A relative humidity as high as 45% can also be used in some cases, though this is normally undesirable. The circulation of the heated air through the cabinet 32 ensures an even temperature throughout the cabinet and even application of the heated air to the upper surface of the mix on the trays 23.

The heating maintains the creamy mix in a viscous liquid state which allows a large part of the entrapped gases to escape during the polymerisation process and consequently prevents the formation of a conventional foam, while accelerating the polymerisation of the material. Due to the fact that the heat is supplied to the mix principally by the heated air passing over its exposed upper surface 15, polymerisation is initiated first in the upper part of the sheet, so that after escape of the aforesaid part of the entrapped gases, a sufficient amount of gas remains trapped by the formation of the dense upper region 14 to produce the cellular region 12. The cells 16 appear to contain principally air entrapped in the mixing step of the process.

Curing of material is completed in approximately 30 minutes, and on removal from the curing cabinet the material is found to have the form illustrated in FIG. 1. The dressing material, still with its release paper backing, is cut into the required shapes and sizes for a medical/surgical wound cover by means of a band knife or roller press and is wrapped in a siliconised tissue and packaged in foil pouches which are sealed and gamma-irradiated to ensure sterile conditions.

Tests have shown that the polymerised dressing material is free from toxic cyanate or amine residues and is highly effective as a wound cover in the treatment of burns. On application to a burn, it conforms to the contour of the wound and absorbs a limited amount of the liquid exudate, while swelling slightly. It is believed that this swelling on contact with liquid causes the cells 16 to open to receive liquid.

In addition to the advantages mentioned above, the dressing material has the specific advantages of resembling skin in texture, of conforming easily and readily to any anatomical contour, and of causing no pain in application. It also has thermal insulation qualities which enable it to maintain an optimum temperature in the wound to promote healing. It is premeable to water vapour and air, so as to permit the passage of gases through it, but being impermeable to liquids it prevents drying and dehydration in or around the wound area. It is non-adherent to wounds, making for painless dressing changes. It does not distort or impede X-ray examination. It is unaffected by contact with antiseptics, and under slight pressure it can act as a haemostat. It will not support bacterial life or growth and it produces no loose fibres or particles which could become embedded or encapsulated in a wound. It requires no soaking before use as with biological wound covers, thus saving valuable nursing time, and it can be applied by any trained nurse without specialised training. The risk of infection is reduced because of the relatively infrequent dressing changes required, and the similarity to skin in texture has a good psychological effect on the patient. The production of a correct micro-climate in the wound increases the speed of healing.

We claim:

1. A wound dressing material, comprising a non-laminated sheet of a synthetic plastics material which is permeable to water vapour and to air and which is impermeable to liquid exudate, said material having on one side a smooth glazed surface for application to a wound, a closed cell cellular region behind the smooth surface, and a more dense region behind the closed cell cellular region, so that on contact with liquid exudate from a wound the dressing material will absorb a limited amount of exudate but prevent it from passing through the dressing material.

2. A dressing material according to claim 1, wherein the synthetic plastics material is a polyurethane which is prepared in the substantial absence of water.

3. A dressing material according to claim 2, wherein the synthetic plastics material is the product of polymerization of an isocyanate capped polyoxyethylene polyol employing a cross-linking agent or catalyst which is reactive with the isocyanate groups.

4. A dressing material according to claim 3, wherein the synthetic plastics material also incorporates an alkylene oxide surfactant to increase the hydrophilic nature of the dressing material.

5. A dressing material according to claim 3, wherein the cross-linking agent or catalyst contains in its molecule two or more amine and/or hydroxyl groups which are reactive with the isocyanate groups.

6. A dressing material according to claim 3, wherein the polyol is a polyoxyethylene diol having a weight average molecular weight of approximately 1500, containing a proportion of polyols having three or more hydroxyl groups, the diol and polyols having been capped with di-isocyanates.

7. A dressing material according to claim 5, wherein the cross-linking agent or catalyst is dimethylethanolamine.

8. A dressing material according to claim 6, wherein the cross-linking agent or catalyst is selected from the group comprising diethylenetriamine, triethylenetetramine, tetraethylenepentamine, polyethyleneimine, glycerol, trimethylolpropane, pentaerythritol, tolylene-2,4,6-triamine, ethylene diamine, amino-ethanol, trimethylenediamine, tetramethylenediamine, pentamethylene-diamine, hexamethylene-diamine, ethanolamine, diethanolamine, hydrazine, triethanolamine, benzene-1,2,4-tricarboxylic acid, nitrilotriacetic acid, citric acid, 4,4'-methylenebis(o-chloroaniline).

9. A dressing material according to claim 4, wherein the alkylene surfactant contains ethylene oxide and propylene oxide.

10. A dressing material according to claim 9, wherein the proportions of ethylene oxide to propylene oxide lie in the range from 75:25% to 40:60% by weight.

* * * * *